United States Patent [19]

Klopping

[11] 4,307,115

[45] Dec. 22, 1981

[54] INSECTICIDAL COMPOSITION

[75] Inventor: Hein L. Klopping, Wilmington, Del.

[73] Assignee: E. I. Du Pont de Nemours and Company, Wilmington, Del.

[21] Appl. No.: 86,048

[22] Filed: Oct. 18, 1979

[51] Int. Cl.$^3$ .................... A01N 33/24; A01N 37/00; A01N 47/10

[52] U.S. Cl. .................................. 424/327; 424/298; 424/300

[58] Field of Search ....................... 424/298, 327, 300

[56] References Cited

U.S. PATENT DOCUMENTS 3,576,834  4/1976  Buchanan ............................ 260/453
3,639,633  2/1972  Buchanan ............................ 424/327

OTHER PUBLICATIONS

Kerr, Chemistry and Industry of Starch (1950), Academic Press, New York, p. 631.
Radley, Industrial Uses of Starch and Its Derivatives, (1976) Applied Science Publishers, Ltd., London p. 239.
"Corn Products Buyers Guide", Englewood, Cliffs, N.J.
"The Pesticide Chemical News Guide", Food Chemistry News, Inc. 12/1/78 p. 112.

Primary Examiner—Allen J. Robinson

[57] ABSTRACT

This invention relates to an insecticidal composition containing methomyl, an anticaking agent, a starch and optionally a wetting and/or dispersing agent and/or a diluent in specified amounts.

24 Claims, No Drawings

INSECTICIDAL COMPOSITION

BACKGROUND OF THE INVENTION

This invention relates to an insecticidal composition. More specifically, this invention relates to an improved methomyl composition.

U.S. Pat. Nos. 3,576,834 and 3,639,633 issued to Buchanan on Apr. 27, 1971 and Feb. 1, 1972, respectively, disclose substituted O-carbamoylhydroxamates, including methomyl, S-methyl-N[(methylcarbamoyl)oxy]thioacetimidate. The compounds are disclosed as being useful in controlling insects and other arthropod pests and are useful in protecting many important food crops against these pests.

Water-dispersible insecticidal compositions are often produced as high strength formulations, i.e., 75-99% by weight of active ingredient, which are diluted at the site of use. It is not uncommon for the dilution to be effected in large tanks of about 100-1000 gallons (378-3780 liters) wherein the only source of agitation is by-pass circulation of the tank contents or a small agitator. Under these rather poor agitation conditions conventional high strength, water-dispersible formulations of methomyl require prolonged periods of time to effect adequate dispersion. Rapid dispersion is an important requirement in commercial pesticide application. In some situations, such as contract aerial applications, time is of the essence. A rapidly dispersible methomyl formulation would greatly assist the applicator in these situations. Thus, a need has developed for a high-strength methomyl formulation with rapid dispersibility.

SUMMARY OF THE INVENTION

There is disclosed a high strength methomyl insecticidal composition consisting essentially of, in percent by weight,
about 75-95%, preferably about 90-94%, of methomyl
about 0.5-4%, preferably about 0.5-3%, of an anticaking agent,
about 2-10%, preferably about 3-7%, of a starch having a Kerr index greater than 10,
about 0-5%, preferably about 0-1%, of a wetting and/or a dispersing agent, and
about 0-22.5%, preferably about 0-6.5%, of a diluent.
The disclosed insecticidal composition of methomyl displays rapid dispersion in cold water under conditions of poor agitation.

DETAILED DESCRIPTION OF THE INVENTION

The composition of the invention contains methomyl, an anticaking agent and a starch having a Kerr index, as hereinafter defined, greater than 10 in the weight percentages previously specified. Optionally, the composition can also contain a wetting and/or a dispersing agent and/or a diluent. In a more preferred embodiment of the invention the composition consists essentially of, in percent by weight,
about 90-94% of methomyl,
about 0.5-3% of an anticaking agent,
about 3-7% of a pregelatinized starch having a Kerr index greater than 10 and having an average particle size such that about 90% will pass through a sieve having 149 micron openings,
about 0-1% of a wetting and/or a dispersing agent, and
about 0-6.5% of a diluent.

Methomyl used in the composition invention can be prepared by processes given in U.S. Pat. No. 3,576,834.

Starches useable in the composition of the invention have a Kerr index greater than 10. The Kerr index is defined as a measure of the water retention of the starch at 25° C. and is determined by the method described on page 143 of "Chemistry and Industry of Starch," edited by Ralph W. Kerr, second edition, Academic Press Inc., New York (1950). In this test water retention of a starch is determined by first wetting 5 g of the starch, measured on a dry solid basis, with a small amount of distilled water to form a dough. Next, more water is added to the dough with stirring to form a suspension which is quantitatively transferred to a 100 ml graduated cylinder. Sufficient water is added to make the total volume of the suspension reach the 100 ml mark on the cylinder. After a complete mixing of the contents, the cylinder is allowed to stand undisturbed for 24 hours at 25° C. At the end of the 24 hour period, the line of demarcation where the starch product appears to have settled out from the water phase is noted. The apparent number of milliliters of the insoluble starch phase divided by 5 is taken as the water retention index, Kerr index, of the starch per gram. Pregelatinized starches, such as "Dura-Jel" starch, "Hi Jel " S starch, "Redisol" 88 starch, "Binasol" 15 starch, all manufactured by A. E. Staley Manufacturing Co., are preferred. In order to avoid pluggage of the nozzle protecting screen on spray application equipment, the starch preferably has an average particle size such that about 90% by weight will pass through a sieve having 149 micron openings. More preferably, the starch has an average particle size such that practically all of it passes through a sieve having 74 micron openings. The starch is present in the composition of the invention in an amount of from about 2-10%, preferably about 3-7% by weight based on the weight of the total composition. Corn starches are preferred for use in the composition of the invention.

Suitable anticaking agents are high-surface-area, low-bulk-density, finely particulate, inert powders. Preferred are amorphous synthetic silicas and more preferred are fumed silicas. Most preferred are fumed silicas with an uncompressed bulk density of about 0.030-0.060 g/ml, a surface area of about 175-330 $m^2$/g, a pH, measured in a 4% aqueous suspension, of about 3.5-4.2, and a nominal particle size of about 0.007-0.014 microns, i.e., the particles of the material range in diameter from about 0.007 to about 0.014 microns. The anticaking agent is present in an amount of about 0.5-4%, preferably 0.5-3% by weight based upon the weight of the total composition.

Surfactants useful in the composition of the invention act as wetting and/or dispersing agents which assist dispersion of the active material in a spray. Suitable wetting agents include such anionic and nonionic agents as have been used heretofore in similar pesticidal compositions. Detailed lists of such agents are given in McCutcheon's "Detergents and Emulsifiers Annual," MC Publishing Co., Ridgewood, N.J. and in Sisely and Wood's "Encyclopedia of Surface Active Agents," Chemical Publishing Co., Inc., New York. Preferred wetting agents are anionic agents, such as sodium alkyl sulfate, sodium alkylarylsulfonates, and sodium dialkyl sulfosuccinates, and nonionic agents, such as polyoxyethylene condensates of phenols, alcohols and organic acids.

Preferred dispersants are alkali and alkaline earth salts of lignosulfonic acids, cellulose ethers, and salts of polymerized alkylarylsulfonates. Surfactants employed herein as dispersing and/or wetting agents can be used in the composition of the invention in an amount of from 0 up to 5% based on the total weight of the resulting insecticidal composition.

Solid diluents which can be used in the composition of the invention are described in Watkins et al., "Handbook of Insecticide Dust Diluents and Carriers," second edition, Dorland Books, Caldwell, N.J. Suitable diluents include those which when put into aqueous suspensions have a pH of less than 8. Preferably, the diluent is a clay which gives an acidic aqueous suspension, such as most kaolinites and some montmorillonites. Synthetic silicas are also useful in this regard. Alkaline clays of the adsorptive type, such as subbentonites, i.e., smectites, can also be used as diluents in the composition of the invention. A diluent is an optional component of the composition of the invention and can be present in an amount of from about 0 to about 22.5%, preferably about 0 to about 6.5% by weight based on the weight of the total composition.

The composition of the invention is made by blending and grinding the ingredients until a product having fine particles and the ingredients thoroughly intermingled is obtained.

Often the user of the composition of the invention will desire to combine it with other pesticides at the time of application. Advantages of such combinations can include control of pests with a smaller total amount of chemicals; control of pairs or communities of pests and pathogens; and regulation of the degree of residual effect.

Pesticides which should be compatible for combination with the composition of the invention include:

Insecticides:
3-hydroxy-N-methylcrotonamide(dimethylphosphate)ester (monocrotophos);
methylcarbamic acid, ester with 2,3-dihydro-2,2-dimethyl-7-benzofuranol (carbofuran);
O-[2,4,5-trichloro-α-(chloromethyl)benzyl]phosphoric acid, O',O'-dimethyl ester (tetrachlorvinphos);
2-mercaptosuccinic acid, diethyl ester S-ester with thionophosphoric acid, dimethyl ester (malathion);
phosphorothioic acid, O,O-dimethyl, O-p-nitrophenyl ester (methylparathion);
methylcarbamic acid, ester with α-naphthol (carbaryl);
N'-(4-chloro-o-tolyl)-N,N-dimethylformamide (chlordimeform);
O,O-diethyl-O-(2-isopropyl-4-methyl-6-pyrimidyl)phosphorothioate (diazinon);
octachlorocamphene (toxaphene);
O-ethyl O-p-nitrophenyl phenylphosphonothioate (EPN)
O,S-dimethylacetylphosphoramidothioate (acephate);
O,O-diethyl-O-3,5,6-trichloro-2-pyridylphosphorothioate (chloropyrifos);
O,O-dimethyl-S-[(4-oxo-1,2,3-benzotriazin-3(4H)-yl)methyl]phosphorodithioate (azinphos-methyl);
S-[(1,3-dihydro-1,3-dioxo-2H-isoindol-2-yl)methyl]-O,O-dimethylphosphorodithioate (phosmet);
6,7,8,9,10,10-hexachloro-1,5,5a,6,9,9a-hexahydro-6,9-methano-2,4,3-benzodioxathiepin 3-oxide (endosulfan);
2-chloro-3-(diethylamino)-1-methyl-3-oxo-1-propenyl dimethylphosphate (phosphamidon);
S-[2-(ethylsulfinyl)ethyl] O,O-dimethylphosphorothioate (oxydemeton-methyl);
O,O-dimethyl S-[2-(methylamino)-2-oxoethyl]phosphorodithioate (dimethoate);
methyl 3-[(dimethoxyphosphinyl)oxy]-2-butenoate (mevinphos);
O,S-dimethyl phosphoramidothioate (methamidophos);
1,1'-(2,2,2-trichloroethylidene)bis[4-methoxybenzene] (methoxychlor);
S-[6-chloro-2-oxo-3(2H)-benzoxazolylmethyl] O,O-diethylphosphorodithioate (phosalone);
mixture of O,O-diethyl O-2-ethylthioethylphosphorothioate and O,O-diethyl S-2-ethylthioethylphosphorothioate (demeton);
dimethyl 2,2,2-trichloro-1-hydroxyethylphosphonate (trichlorphon);
(S)-α-cyano-3-phenoxybenzyl (1R)-cis-3-(2,2-dibromovinyl)-2,2-dimethylcyclopropane carboxylate (decamethrin);
α-cyano-3-phenoxybenzyl-2,2-dimethyl-3-(2,2-dichlorovinyl)cyclopropanecarboxylate (cypermethrin);
α-cyano(3-phenoxyphenyl)-methyl-4-chloro-α-(1-methylethyl)benzeneacetate (fenvalerate);
(3-phenoxyphenyl)methyl(+)-cis,trans-3-(2,2-dichloroethenyl)-2,2-dimethylcyclopropanecarboxylate (permethrin);
O-(4-bromo-2-chlorophenyl)-O-ethyl-S-propylphosphorothioate (profenofos); and
phosphorothiolothionic acid, O-ethyl-O-[4-(methylthio)phenyl]-S-n-propyl ester ("Bolstar").

Fungicides:
methyl 2-benzimidazolecarbamate (carbendazim);
tetramethyl thiuram disulfide (thiram);
n-dodecylguanidine acetate (dodine);
manganese ethylenebisdithiocarbamate (maneb);
1,4-dichloro-2,5-dimethoxybenzene (chloroneb);
methyl 1-(butylcarbamoyl)-2-benzimidazolecarbamate (benomyl);
2-cyano-N-ethylcarbamoyl-2-methoxyiminoacetamide ("Curzate");
N-trichloromethylthiotetrahydrophthalimide (captan);
N-trichloromethylthiophthalimide (folpet);
dimethyl [1,2-phenylenebis(iminocarbonothionyl)]biscarbamate (thiophanate methyl);
2,4,5,6-tetrachloro-1,3-benzenedicarbonitrile (chlorothalonil);
triphenyltin hydroxide (fentin hydroxide); and
3a,4,7,7a-tetrahydro-2-(1,1,2,2-tetrachloroethyl) thio-1H-isoindole-1,3(2H)-dione (captafol).

Nematicides:
S-methyl 1-(dimethylcarbamoyl)-N-(methylcarbamoyloxy)-thioformimidate (oxamyl);
N-isopropylphosphoramidic acid, O-ethyl-O'-[4-(methylthio)-m-tolyl]diester (phenamiphos);

Bactericides:
tribasic copper sulfate; and
streptomycin sulfate

Acaricides:
2-(1-methylpropyl)-4,6-dinitrophenyl 3-methyl-2-butenoate (binapacryl);
6-methyl-1,3-dithiolo[4,5—b]quinoxalin-2-one (quinomethionate);
ethyl 4,4'-dichlorobenzilate (chlorobenzilate)
2-[4-(1,1-dimethylethyl)phenoxy]-cyclohexyl-2-propynyl sulfite (propargite);
1,1',2,2',3,3',4,4',5,5'-decachloro-bis-2,4-cyclopentadien-1-yl (dienochlor);

1,1-bis(p-chlorophenyl)-2,2,2-trichloroethanol (dicofal), and tricyclohexyltin hydroxide (cyhexatin).

Microorganism:

Bac. Thuringiensis (dipel)

The invention is further illustrated by the following examples in which all percentages are by weight unless otherwise specified. In the examples the dispersibility of a composition is measured by two different tests which are called the aquarium test and the tablet disintegration test.

Aquarium Test

Approximately 26 liters of water at 10° C. are placed in a 30×50×25 cm aquarium. An 800 rpm stirrer with a rectangular, straight blade (1.8×7.7 cm) is placed in one corner of the aquarium so that the blade is 2 cm from the bottom and the sides of the aquarium. In the opposite corner is placed a cage having dimensions of about 13×10×13 cm and made from galvanized metal gauze with 6 mm square openings. The cage is open-ended and protrudes about 6 cm above the water surface.

Twenty-five grams of the composition to be tested are packaged in an approximately 7.5×5.5 cm envelope of cold-water-soluble bag material. The envelope is sealed and then placed on the surface of the water within the confines of the cage. When the bag material dissolves, the composition while retaining its rectangular shape becomes wet throughout and sinks to the bottom of the aquarium. Immediately after the material reaches the bottom, the stirrer is started and the time required for the rectangularly-shaped lump of material to become completely dispersed is measured. Only tests in which the rectangularly-shaped mass of material remains intact until it settles to the bottom are used to evaluate the composition.

TABLET DISINTEGRATION TEST

Ten grams of the composition to be tested are pressed to form a tablet with a diameter of about 4.5 cm and a thickness of about 1.1 cm by using a pressure of approximately 9,000 lbs/in$^2$ (630 kg/cm$^2$) in a suitable press. Five hundred milliliters of water at 10° C. is placed in a cylindrical glass jar having a diameter of about 9 cm and a height of 16.5 cm. The tablet is dropped into the jar and the time required for the tablet to disintegrate into a snow-like pile of material is measured.

In the aquarium test, a composition of the invention is dispersed in about 3-8 minutes whereas a conventional methomyl formulation requires about 20 minutes to become dispersed. In the tablet disintegration test, a composition of the invention breaks-up in about 6-8 minutes or less whereas a conventional methomyl formulation does not disintegrate after 2 hours and often not even after standing overnight.

EXAMPLE 1

A composition of the invention is prepared from the following ingredients:

| | |
|---|---|
| Methomyl | 91.0% |
| Fumed silica | 2.0% |
| Starch | 7.0% |

The starch is pregelatinized "Dura-Jel" starch, has a Kerr index of greater than 20, and 100% of its passes through a sieve having 74 micron openings. The ingredients are thoroughly blended and passed through a sieve having 420 micron openings. Material which does not pass through the sieve is ground in a mortar until it does pass through. All the material is combined and reblended. This product disperses completely in less than 3 minutes and in 5.5 minutes in the aquarium and tablet disintegration tests, respectively.

EXAMPLE 2

A composition of the invention is prepared from the following ingredients:

| | |
|---|---|
| Methomyl | 91.0% |
| Fumed silica | 2.0% |
| Sodium dioctyl sulfosuccinate | 0.2% |
| Pregelatinized "Dura-Jel" starch having a Kerr index of 20 and 100% passing through a sieve with 74 micron openings | 6.8% |

The ingredients are thoroughly blended and screened through a sieve having 420 micron openings. The portion of the material which does not pass through the sieve is hammer-milled so that practically all of it does pass through. All fractions passing through the sieve are recombined and reblended. This product disperses completely in less than 6 minutes in both the aquarium and tablet disintegration tests.

EXAMPLE 3

A composition of the invention is prepared from the following ingredients:

| | |
|---|---|
| Methomyl | 91.0% |
| Fumed silica | 2.0% |
| Sodium dioctyl sulfosuccinate | 0.2% |
| Methyl cellulose | 0.1% |
| Pregelatinized starch | 6.7% |

The starch is "Hi-Jel" S, has a Kerr index of 13 and 100% of it passes through a sieve having 74 micron openings. The methyl cellulose has a viscosity of 13-19 cps for a solution of 2% in water at 20° C. as measured by ASTM method D1347. The ingredients are blended and ground using a procedure similar to that described in Example 2. The resulting product disperses completely in about 6 minutes in the aquarium test.

EXAMPLE 4

A composition of the invention is prepared from the following ingredients:

| | |
|---|---|
| Methomyl | 96.0% |
| Fumed silica | 0.5% |
| Pregelatinized starch | 3.5% |

The starch is "Binasol" 15 starch, has a Kerr index of 12.5 and 100% of its passes through a sieve having 74 micron openings. The ingredients are blended and ground using a procedure similar to that described in Example 1. In the aquarium test this product disperses completely in 7.75 minutes.

EXAMPLE 5

A composition of the invention can be prepared from the following ingredients:

| | |
|---|---|
| Methomyl | 77.0% |
| Fumed silica | 4.0% |
| Sodium lauryl sulfonate | 3.0% |
| Sodium salt of polymerized alkylarylsulfonic acid | 2.0% |
| Pregelatinized starch with a Kerr index >20 | 10.0% |
| Kaolinite | 4.0% |

Ninety percent of the starch, which is "Redisol" 88, should pass through a sieve having 149 micron openings. The ingredients can be blended and hammer-milled using a procedure similar to that described in Example 2.

In the aquarium and tablet disintegration tests, this product should give results similar to those obtained in the preceding examples.

EXAMPLE 6

A composition of the invention can be prepared from the following ingredients:

| | |
|---|---|
| Methomyl | 75.0% |
| Fumed silica | 2.0% |
| Sodium alkylnaphthalene sulfonate | 2.0% |
| Sodium lignosulfonate | 1.0% |
| Pregelatinized starch | 5.0% |
| Synthetic silica | 15.0% |

The starch is similar to that used in Example 1. The ingredients can be blended and ground to give material which predominantly passes through a sieve having 250 micron openings. In the aquarium and tablet disintegration tests, this product should give results similar to those obtained in the preceding examples.

EXAMPLE 7

A composition of the invention can be prepared from the following ingredients:

| | |
|---|---|
| Methomyl | 85.0% |
| Fumed silica | 1.5% |
| Sodium alkylarylsulfonate | 0.3% |
| Pregelatinized starch | 10.0% |
| Sub-bentonite | 3.2% |

The starch has a Kerr index greater than 12 and 90% of its passes through a screen having 105 micron openings. The ingredients can be thoroughly blended and hammer-milled using a procedure similar to that described in Example 2. In the aquarium and tablet disintegration tests this product should give results similar to those obtained in the preceding examples.

EXAMPLE 8

A composition of the invention can be prepared from the following ingredients:

| | |
|---|---|
| Methomyl | 75.0% |
| Sodium dioctylsulfosuccinate | 0.1% |
| Fumed silica | 0.5% |
| Pregelatinized starch | 4.0% |
| Kaolinite | 20.4% |

The starch is similar to that used in Example 1. The ingredients can be blended and ground using a procedure similar to that described in Example 1. The resulting product would give, in the aquarium and tablet disintegration tests, dispersing times similar to those obtained in the preceding examples.

What is claimed is:

1. An insecticidal composition consisting essentially of
   about 75–95% of methomyl,
   about 0.5–4% of an anticaking agent,
   about 2–10% of a pregelatinized starch having a Kerr index greater than 10,
   about 0–5% of a wetting agent, a dispersing agent or mixture thereof, and
   about 0–22.5% of a diluent,
   said percentages being by weight.

2. A composition of claim 1 having 90–94% by weight of methomyl.

3. A composition of claim 1 having 3–7% by weight of starch.

4. A composition of claim 1 wherein the starch is pregelatinized and has a particle size such that about 90% by weight of said starch will pass through a sieve having openings of 149 microns.

5. A composition of claim 1 having 0.5–3% by weight of anticaking agent.

6. A composition of claim 4 wherein the starch has a particle size such that practically all of it passes through a sieve having openings of 74 microns.

7. A composition of claim 2 having 3–7% by weight of starch.

8. A composition of claim 7 wherein the starch is pregelatinized and has a particle size such that about 90% by weight of said starch will pass through a screen having openings of 149 microns.

9. A composition of claim 8 having 0.5–3% by weight of a fumed silica as an anticaking agent.

10. A composition of claim 9 having 0–1% by weight of wetting agent, dispersing agent or mixture thereof.

11. A composition of claim 10 having 0–6.5% by weight of diluent.

12. A composition of claim 11 wherein the starch has a particle size such that practically all of it passes through a sieve having openings of 74 microns.

13. A method of controlling insects comprising applying to a locus to be protected an insecticidally effective amount of a composition of claim 1.

14. A method of controlling insects comprising applying to a locus to be protected an insecticidally effective amount of a composition of claim 2.

15. A method of controlling insects comprising applying to a locus to be protected an insecticidally effective amount of a composition of claim 3.

16. A method of controlling insects comprising applying to a locus to be protected an insecticidally effective amount of a composition of claim 4.

17. A method of controlling insects comprising applying to a locus to be protected an insecticidally effective amount of a composition of claim 5.

18. A method of controlling insects comprising applying to a locus to be protected an insecticidally effective amount of a composition of claim 6.

19. A method of controlling insects comprising applying to a locus to be protected an insecticidally effective amount of a composition of claim 7.

20. A method of controlling insects comprising applying to a locus to be protected an insecticidally effective amount of a composition of claim 8.

21. A method of controlling insects comprising applying to a locus to be protected an insecticidally effective amount of a composition of claim 9.

22. A method of controlling insects comprising applying to a locus to be protected an insecticidally effective amount of a composition of claim 10.

23. A method of controlling insects comprising applying to a locus to be protected an insecticidally effective amount of a composition of claim 11.

24. A method of controlling insects comprising applying to a locus to be protected an insecticidally effective amount of a composition of claim 12.

* * * * *